United States Patent [19]

Lee et al.

[11] Patent Number: 5,767,311

[45] Date of Patent: Jun. 16, 1998

[54] METHOD AND APPARATUS FOR PREPARING PURIFIED TEREPHTALIC ACID

[75] Inventors: Fu-Ming Lee; Wei-Teh Wade Shang, both of Katy, Tex.

[73] Assignee: Glitsch International, Inc.

[21] Appl. No.: 477,898

[22] Filed: Jun. 7, 1995

[51] Int. Cl.[6] .................................................. C07C 51/487
[52] U.S. Cl. .......................... 562/487; 562/485; 562/414; 562/483; 562/409
[58] Field of Search ................................. 562/409, 483, 562/487

[56] References Cited

U.S. PATENT DOCUMENTS

| | | | |
|---|---|---|---|
| 2,636,899 | 4/1953 | Burrows et al. | 260/524 |
| 2,833,816 | 5/1958 | Saffer et al. | 260/524 |
| 2,833,817 | 5/1958 | Saffer et al. | 260/524 |
| 2,891,992 | 6/1959 | Raecks et al. | 260/515 |
| 2,905,709 | 9/1959 | Scheak et al. | 260/515 |
| 2,923,736 | 2/1960 | Maclean | 260/525 |
| 2,949,483 | 8/1960 | Ham | 260/516 |
| 3,330,863 | 7/1967 | Read et al. | 260/525 |
| 3,388,156 | 6/1968 | Sakurai et al. | 260/525 |
| 3,431,296 | 3/1969 | Ichikawa et al. | 260/525 |
| 3,465,035 | 9/1969 | Nakaguchi et al. | 260/525 |
| 3,497,552 | 2/1970 | Olsen | 260/525 |
| 3,574,727 | 4/1971 | Taylor et al. | 260/525 |
| 3,584,039 | 6/1971 | Meyer | 260/525 |
| 3,766,257 | 10/1973 | Wimer et al. | 260/515 |
| 3,766,258 | 10/1973 | Engelbrecht et al. | 260/515 |
| 3,859,344 | 1/1975 | Shigeyasu et al. | 260/524 |
| 3,953,502 | 4/1976 | Fassell et al. | 260/525 |
| 4,053,506 | 10/1977 | Park et al. | 260/525 |
| 4,081,464 | 3/1978 | Marsh et al. | 260/524 |
| 4,165,337 | 8/1979 | Yoshinaka et al. | 260/544 |
| 4,197,412 | 4/1980 | Kimura et al. | 562/416 |
| 4,201,871 | 5/1980 | Tanouchi et al. | 562/486 |
| 4,201,872 | 5/1980 | Kimura et al. | 562/487 |
| 4,228,299 | 10/1980 | Ferguson et al. | 560/124 |
| 4,230,882 | 10/1980 | Seko et al. | 562/416 |
| 4,245,078 | 1/1981 | Suzuki et al. | 562/412 |
| 4,260,817 | 4/1981 | Thompson et al. | 562/487 |
| 4,263,452 | 4/1981 | Komatsu et al. | 562/487 |
| 4,268,690 | 5/1981 | Komatsu et al. | 562/416 |
| 4,275,230 | 6/1981 | Donaldson | 562/486 |
| 4,281,179 | 7/1981 | Komatsu et al. | 562/416 |
| 4,286,101 | 8/1981 | Hashizume et al. | 562/487 |
| 4,297,507 | 10/1981 | Komatsu et al. | 562/416 |
| 4,314,073 | 2/1982 | Crooks | 562/416 |
| 4,317,923 | 3/1982 | Imai | 562/487 |
| 4,331,824 | 5/1982 | Ikeda et al. | 585/638 |
| 4,334,090 | 6/1982 | Donaldson | 562/480 |
| 4,340,752 | 7/1982 | List et al. | 562/485 |
| 4,345,089 | 8/1982 | Nagura et al. | 560/77 |
| 4,357,475 | 11/1982 | Hanotier et al. | 562/414 |
| 4,380,662 | 4/1983 | Hanotier et al. | 562/486 |
| 4,415,479 | 11/1983 | Puskas et al. | 502/85 |
| 4,438,279 | 3/1984 | Packer et al. | 562/416 |
| 4,447,646 | 5/1984 | Johnson et al. | 562/487 |
| 4,459,418 | 7/1984 | Greenshields | 549/370 |
| 4,467,110 | 8/1984 | Puskas et al. | 562/487 |
| 4,467,111 | 8/1984 | Puskas et al. | 562/487 |
| 4,485,244 | 11/1984 | Fox et al. | 549/245 |
| 4,490,554 | 12/1984 | Tanaka et al. | 562/486 |
| 4,500,732 | 2/1985 | Petty-Weeks et al. | 562/486 |
| 4,537,980 | 8/1985 | Greenshields | 549/370 |
| 4,540,493 | 9/1985 | Dickerson et al. | 210/669 |
| 4,605,763 | 8/1986 | Kiefer et al. | 562/487 |
| 4,625,059 | 11/1986 | Shibano et al. | 562/600 |
| 4,626,598 | 12/1986 | Packer et al. | 562/487 |
| 4,629,715 | 12/1986 | Schroeder | 502/185 |
| 4,652,674 | 3/1987 | James et al. | 562/414 |
| 4,675,108 | 6/1987 | Dickerson et al. | 210/275 |
| 4,675,438 | 6/1987 | Schwartz et al. | 562/416 |
| 4,728,630 | 3/1988 | Schroeder et al. | 502/185 |
| 4,772,748 | 9/1988 | Hashizume et al. | 562/413 |
| 4,782,181 | 11/1988 | James | 562/487 |
| 4,791,226 | 12/1988 | Puskas et al. | 562/487 |
| 4,808,751 | 2/1989 | Schroeder et al. | 562/487 |
| 4,827,026 | 5/1989 | Brugge et al. | 562/416 |
| 4,833,269 | 5/1989 | Schroeder | 562/484 |
| 4,877,900 | 10/1989 | Tamaru et al. | 562/413 |
| 4,886,901 | 12/1989 | Holzhauer et al. | 560/77 |
| 4,892,972 | 1/1990 | Schroeder et al. | 562/487 |
| 4,933,491 | 6/1990 | Albertins et al. | 562/416 |
| 4,933,492 | 6/1990 | Schroeder et al. | 562/487 |
| 4,937,378 | 6/1990 | Schroeder | 562/487 |
| 4,939,297 | 7/1990 | Browder et al. | 562/485 |
| 4,948,921 | 8/1990 | Green et al. | 562/413 |

(List continued on next page.)

OTHER PUBLICATIONS

Tr. Vses. Nauch.–Issled. Proekt. Inst. Monomerov (1970), 2(2), 26–32; From: Ref. Zh., Khim. 1971, Abstr. No. 1N166; V.N. Kulakov, et al.; "Purification of Aromatic Dicarboxylic Acids Obtained by Liquid–Phase Oxidation of Dialkyl Derivatives of Aromatic Hydrocarbons".

Kulakov et al ;ZH.,Khim. Abstr. No. 1N166, 1971.

*Primary Examiner*—C. Warren Ivy
*Assistant Examiner*—Sreeni Padmanabhan
*Attorney, Agent, or Firm*—Jenkens & Gilchrist, P.C.

[57] ABSTRACT

A method and apparatus for purifying crude terephthalic acid from a liquid dispersion thereof also containing impurities selected from unreacted starting materials, solvents, products of side reactions and/or other undesired materials is provided. The method comprises the steps of filtering the dispersion to form a crude terephthalic acid filter cake, dissolving the filter cake in a selective crystallization solvent at an elevated temperature to form a solution, crystallizing purified terephthalic acid from the solution in the crystallization solvent by reducing the temperature of the solution, and separating the crystallized purified terephthalic acid from the solution. According to the invention, the selective crystallization solvent is non-aqueous, non-corrosive and essentially non-reactive with terephthalic acid. Preferably, the selective crystallization solvent is N-methyl pyrrolidone. The method and apparatus produces purified terephthalic acid having a purity desired for use in forming polyester resin and other products at an economically attractive rate and at operating conditions of reduced severity which require a lower capital investment and simplified processing.

33 Claims, 3 Drawing Sheets

U.S. PATENT DOCUMENTS

| | | | |
|---|---|---|---|
| 5,068,410 | 11/1991 | Tanaka et al. | 562/483 |
| 5,095,144 | 3/1992 | Sato et al. | 562/481 |
| 5,095,145 | 3/1992 | Rosen | 562/483 |
| 5,095,146 | 3/1992 | Zeitlin et al. | 562/486 |
| 5,097,066 | 3/1992 | Holzhauer et al. | 562/487 |
| 5,107,020 | 4/1992 | Reeve | 562/416 |
| 5,110,984 | 5/1992 | Janulis | 562/487 |
| 5,113,015 | 5/1992 | Palmer et al. | 562/608 |
| 5,132,450 | 7/1992 | Tanaka et al. | 562/414 |
| 5,159,109 | 10/1992 | Rosen et al. | 562/509 |
| 5,166,420 | 11/1992 | Shiraki et al. | 562/487 |
| 5,169,977 | 12/1992 | Tanaka et al. | 560/78 |
| 5,175,352 | 12/1992 | Iwane et al. | 562/417 |
| 5,175,355 | 12/1992 | Streich et al. | 562/485 |
| 5,183,933 | 2/1993 | Harper et al. | 562/414 |
| 5,189,209 | 2/1993 | Ohta et al. | 562/414 |
| 5,200,557 | 4/1993 | Gee et al. | 562/486 |
| 5,254,719 | 10/1993 | Holzhauer et al. | 560/78 |
| 5,256,817 | 10/1993 | Sikkenga et al. | 562/487 |
| 5,292,934 | 3/1994 | Sikkenga et al. | 562/413 |
| 5,304,676 | 4/1994 | Hindmarsh et al. | 562/414 |
| 5,306,845 | 4/1994 | Yokohama et al. | 568/484 |
| 5,344,969 | 9/1994 | Iwane et al. | 562/486 |
| 5,354,898 | 10/1994 | Schroeder | 562/485 |
| 5,362,908 | 11/1994 | Schroeder et al. | 562/487 |

METHOD AND APPARATUS FOR PREPARING PURIFIED TEREPHTALIC ACID

The present invention relates to a method and apparatus for preparing purified terephthalic acid. It also relates to methods and apparatuses for purifying crude terephthalic acid to produce a purified terephthalic acid product which is a useful starting material for producing polyester resin, which is in turn useful for the production of fibers, film, plastic bottles, and polyester resin structures, often reinforced by other materials such as glass fiber.

BACKGROUND OF THE INVENTION

Purified terephthalic acid (PTA) is a starting material for the formation of polyester resin, which is, in turn, used to make many materials of commerce having a variety of utilities. Purified terephthalic acid is formed from "crude" terephthalic acid conventionally by a number of purification methods, often with the aid of catalysts. The methods for purifying crude terephthalic acid heretofore available are not completely satisfactory either from an engineering standpoint, or from an economic standpoint, yet the purity of the purified terephthalic acid is an important determinant of the satisfactoriness of the processes by which the polyester resin is formed.

A number of reaction systems are known for forming crude terephthalic acid from a variety of starting materials. The purification aspects of the present invention may be used with substantially any of these reaction systems, but in accordance with the invention it is preferred that a reaction system involving the oxidation of paraxylene (p-xylene) be employed, and the use of such a synthesis system forms a part of the present invention.

The problems of existing and prior systems for producing purified terephthalic acid center around the difficulties in running the reaction systems to produce good yields of crude terephthalic acid economically, compounded by the difficulties of refining the crude terephthalic acid to eliminate impurities and unwanted components to produce purified terephthalic acid of a quality suitable as a starting material for producing polyester. Concomitant problems in prior systems include the high capital investment required for PTA plants, the severity of operating conditions of prior processes, both for the production of crude terephthalic acid, and for its purification, and the need for handling catalyst systems and reaction solvents, as well as reaction byproducts in a way such that environmental problems are minimized, and loss of material is also controlled.

SUMMARY OF THE INVENTION

In accordance with the present invention there is provided a method and apparatus for producing purified terephthalic acid. In one aspect, the method includes the production of crude terephthalic acid by the oxidation of p-xylene. The oxidation step produces not only terephthalic acid, but by side reactions p-toluic acid and 4-carboxybenzaldehyde (4-CBA). The product produced in the oxidation step is a liquid dispersion containing unreacted starting materials, solvents, if any have been used, the products of side reactions, particularly those just mentioned, and other materials which are not desired in the sought-for purified terephthalic acid. The oxidation step of the present invention is so conducted that the conversion to crude terephthalic acid should be at least about 30% by weight per pass of p-xylene.

In further accordance with the invention, the crude terephthalic acid from the oxidizer is first grossly separated from the other materials from the oxidizer and then it is re-dissolved in a selective crystallization solvent and, optionally, one or more additional solvents of the invention discussed below. The re-dissolved crude terephthalic acid is then crystallized out of the selective crystallization solvent and additional solvents of the invention in one or, preferably, two crystallization stages. Provision is made to separate out the crystallized and progressively purified terephthalic acid from the solvents of the invention, and the filter cake of purified terephthalic acid ultimately obtained is washed with other solvents of the invention and ultimately dried for storage or for further processing.

The invention also contemplates that steps are included to reclaim and recycle the solvents of the invention at each stage of crystallization and washing, including recycle of some of the recovered materials to the oxidizer. Steps are also taken to closely control the delivery of any objectionable materials to the environment.

In an important aspect, the present invention is based on several discoveries relating to solvents which are effective to bring about the purification of crude terephthalic acid through crystallization and separation steps. These discoveries may be summarized in several ways as follows.

Figure 2:
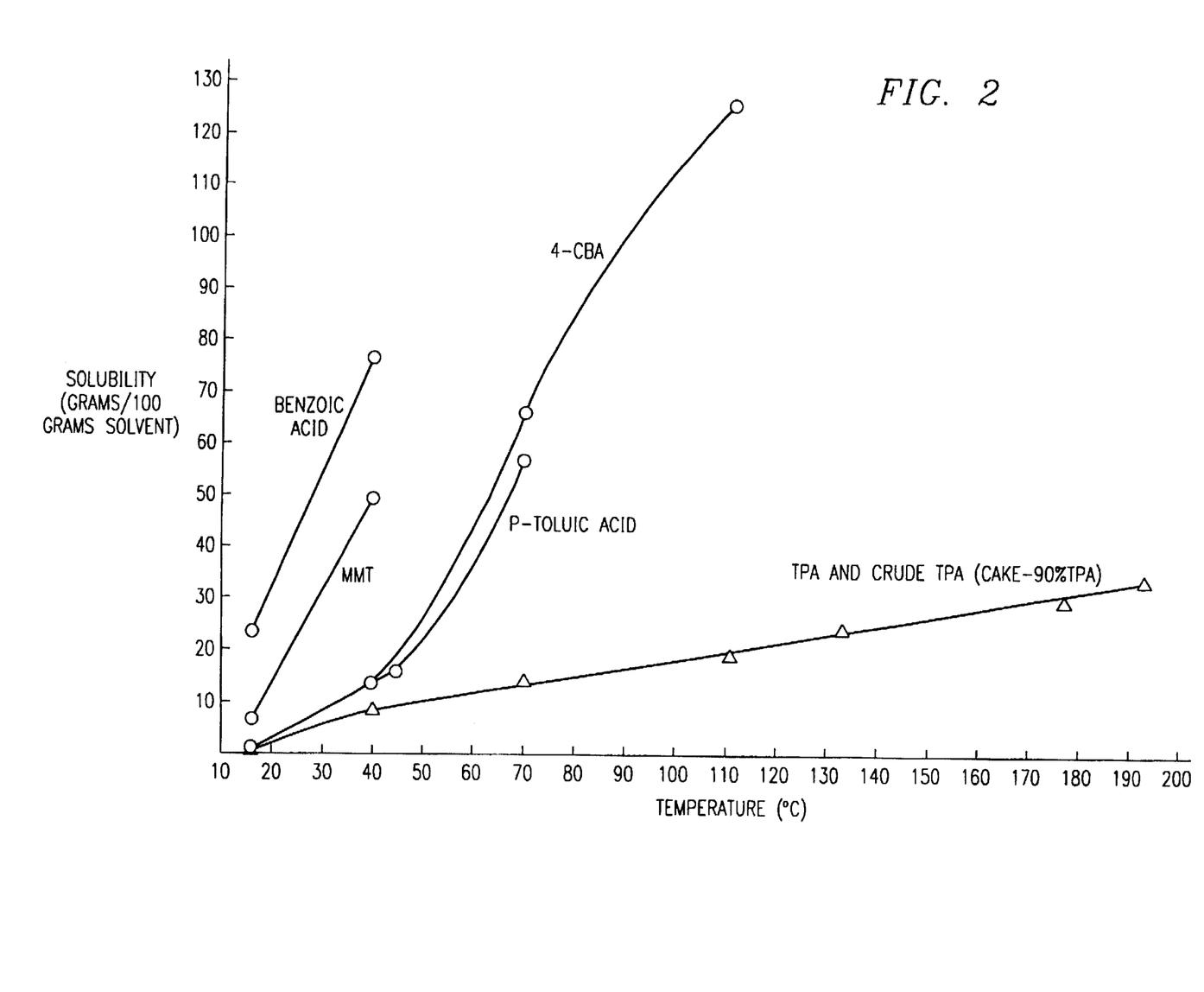
FIG. 2 is a plot of solubility versus temperature curves for terephthalic acid and for impurities or side reaction products commonly associated with crude terephthalic acid.

The selective crystallization solvents useful in the practice of the present invention include those in which (a) the impurities desired to be separated from terephthalic acid to purify it are relatively more soluble in the solvent than is the terephthalic acid at substantially every temperature within the desired range of temperatures at which the solvent containing terephthalic acid is to be handled, and (b) the terephthalic acid is more soluble at an elevated temperature and less soluble at a lower or reduced temperature. It is to be understood that the term "selective crystallization solvent" is intended to mean solvents useful in the selective crystallization of terephthalic acid as described above and as described in greater detail below and as shown in FIG. 2.

In this connection it should be noted that U.S. Pat. No. 3,465,035 mentions that certain organic solvents (pyridine, dimethyl sulfoxides, dimethyl foramide, and the like) have been used to purify terephthalic acid, but that they suffer from being unstable in air and easily form addition products with terephthalic acid. This same patent, along with several others, also teaches the use of acetic acid and water as purification solvents for terephthalic acid. By contrast, the selective crystallization solvents according to the present invention are (a) non-aqueous, (b) non-corrosive, and (c) essentially non-reactive with terephthalic acid and do not include those prior practices just described. Specifically, water, acetic (and other alkyl) acid, and the above-mentioned organic solvents are excluded from the selective crystallization solvents which are contemplated by the present invention.

In accordance with the invention, the primary preferred selective crystallization solvent is N-methyl pyrrolidone (NMP), for the several reasons discussed below, and for its superior performance.

N-methyl pyrrolidone (NMP) is the most preferred selective crystallization solvent for the practice of the invention. It is non-aqueous, thermally stable, nontoxic (environmentally safe), non-corrosive, and commercially available. NMP is the preferred selective crystallization solvent for the practice of the present invention, because its solubility versus temperature curve for terephthalic acid slopes upwardly and to the right, which means that terephthalic acid can be dissolved in it at elevated temperatures, and precipitated or crystallized from it at lower temperatures.

Although NMP is the most preferred selective crystallization solvent, it is to be understood that, in accordance with the present invention, other preferred selective crystallization solvents for purification of crude terephthalic acid can be selected from various polar organic solvents including, but not intended to be limited to, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), and N-hydroxyalkyl-2-pyrrolidone (such as N-hydroxyethyl-2-pyrrolidone), and the like, and mixtures thereof. Still other selective crystallization solvents contemplated by the present invention include, but are not intended to be limited to, sulfolane, methyl sulfolane, the sulfones, the morpholines (such as, morpholine and N-formyl morpholine), the carbitols, $C^1$ to $C^{12}$ alcohols, the ethers, the amines, the amides, and the esters, and the like, and mixtures thereof.

It is preferred that the desired selective crystallization solvent be used in a multi-stage crystallization process in combination with one or more additional solvents, preferably two such additional solvents, particularly where the crude terephthalic acid is less than about 98% pure. Preferably, a wash solvent, such as, but not intended to be limited to, p-xylene, acetone, methyl ethyl ketone (MEK) or methanol, and the like, is used in the washing of the initial filter cake obtained from the first separation of crude terephthalic acid from other materials issuing from the oxidizer. In addition, a displacement solvent having a low boiling point, such as, but not intended to be limited to, methanol, acetone, MEK, and the like, may be used. Preferably, methanol, is used as the displacement solvent in association with the third filter following the second crystallization stage in the preferred process. The desired displacement solvent displaces the selective crystallization solvent from the resulting filter cake, whereby substantially only the displacement solvent is present during the drying process. It is to be understood that the low boiling point of the displacement solvent facilitates the drying of the filter cake.

As described above, NMP is the most preferred selective crystallization solvent for the practice of the invention. It is non-aqueous, thermally stable, nontoxic (environmentally safe), non-corrosive, and commercially available. NMP is the preferred selective crystallization solvent for the practice of the present invention, because, among other things, its solubility versus temperature curve for terephthalic acid slopes upwardly and to the right, which means that terephthalic acid can be dissolved in it at elevated temperatures, and precipitated or crystallized from it at lower temperatures. However, the solubility versus temperature curve for terephthalic acid is of a much milder slope than the solubility curves in NMP for other materials sought to be separated from crude terephthalic acid, such as benzoic acid, 4-carboxybenzaldehyde (4-CBA), and p-toluic acid. As a consequence, when crude terephthalic acid, containing or associated with unreacted starting materials, solvents (if any), and products of side reactions, such as those mentioned above, or other undesired materials, is dissolved in NMP at an elevated temperature, substantially all the materials are dissolved or at least highly dispersed. Then upon removal of heat and cooling of the NMP solution of such dissolved materials, the pure terephthalic acid preferentially crystallizes out, while the other more soluble materials which may be regarded as impurities for the present purposes remain in solution in NMP. A separation is thus effected between purified terephthalic acid and its associated impurities. NMP may be stripped of the impurities in a reclaiming column and recycled into the process, while the impurities may be recycled to the oxidizer step or otherwise disposed of.

From the foregoing, it can be seen that in accordance with one aspect of the present invention, a method is provided for producing purified terephthalic acid from crude terephthalic acid in which the crude terephthalic acid is dissolved in a desired crystallization solvent at an elevated temperature to form a solution and further, in which a purified terephthalic acid is crystallized from that solution at a reduced temperature.

In accordance with another aspect of the invention, a method and apparatus are provided for purifying crude terephthalic acid from a liquid dispersion thereof also containing unreacted starting materials, solvents, products of side reactions, and/or other undesired materials in which the crude terephthalic acid is filtered from that dispersion to partially separate it from the other materials contained therein by filtration to produce a crude terephthalic acid filter cake, and then dissolving that filter cake in a desired selective crystallization solvent at an elevated temperature to form a solution. Purified terephthalic acid is crystallized from that solution by reducing the temperature thereof and is separated from the solvent following crystallization.

In accordance with still another aspect of the invention, a method and apparatus are provided for producing purified terephthalic acid from crude terephthalic acid by dissolving the crude terephthalic acid in a desired selective crystallization solvent at an elevated temperature to form a first solution. First stage purified terephthalic acid is crystallized from that first solution at a reduced temperature. The first stage purified terephthalic acid is separated from the solvent solution of other impurities and redissolved in the desired selective crystallization solvent at an elevated temperature to form a second solution. This second solution is crystallized at a reduced temperature to form a second stage purified terephthalic acid and the second stage purified terephthalic acid is separated from the second solution.

In accordance with yet another aspect of the invention, crude terephthalic acid is synthesized by contacting paraxylene with oxygen in an oxidizer reaction. The crude terephthalic acid is withdrawn from the oxidizer and separated grossly from the side products of the reaction, and unreacted starting materials. The separated crude terephthalic acid is then dissolved in a desired selective crystallization solvent at an elevated temperature and crystallized from it as purified terephthalic acid at a reduced temperature. More than one stage of dissolving in a desired selective crystallization solvent at an elevated temperature followed by crystallization at a reduced temperature, with accompanying separation and washing of the crystallized purified terephthalic acid, may be performed.

From the foregoing, it can be seen that an object of the present invention to provide an improved method and apparatus for producing purified terephthalic acid of a purity desired for use in forming polyester resin and other products, at an economically attractive rate, and at operating conditions of reduced severity which require a lower capital investment and simplified processing. The manner in which these and other objects of the invention are attained may be learned by consideration of the detailed description of the invention which follows, together with the accompanying drawings.

BRIEF DESCRIPTION OF THE DRAWINGS

A more complete understanding of the method and apparatus of the present invention may be obtained by reference to the following Detailed Description when taken in conjunction with the accompanying Drawings wherein:

FIGS. 1A and 1B are simplified flow diagrams of an apparatus with which the method according to the invention may be practiced wherein FIG. 1A is that portion of the apparatus for performing the first stage crystallization steps and wherein FIG. 1B is that portion of the apparatus for performing the second stage crystallization steps.

DETAILED DESCRIPTION OF EMBODIMENTS

I. Process Description

The present invention relates to the development of a new PTA manufacturing technology. Compared to the current widely used PTA technology, this technology provides a substantially lower capital investment in new PTA plant construction, as well as lower costs of plant operation. It also provides means for current DMT plants to co-produce PTA, to strengthen their competitiveness against newer PTA plants.

Process Summary

The success of this process is based on the development of a low pressure, low temperature, non-aqueous, highly selective crystallization technology. The crystallization technology can purify the crude terephthalic acid (TA) with purity as low as from between about 70% (from the oxidizer) and about 98+% in the first-stage crystallizer, and about 99.99+% in the second-stage crystallizer. This allows the TA oxidizer to be operated at much lower severity than those of widely used prior art processes. No acetic acid (as solvent/ diluent) or bromine-catalyst initiator is needed in the oxidizer in accordance with the present invention. The selective crystallization solvent used in the crystallization process is non-aqueous, thermally stable, non-toxic (environmentally safe), non-corrosive, and commercially available.

Figure 1A:
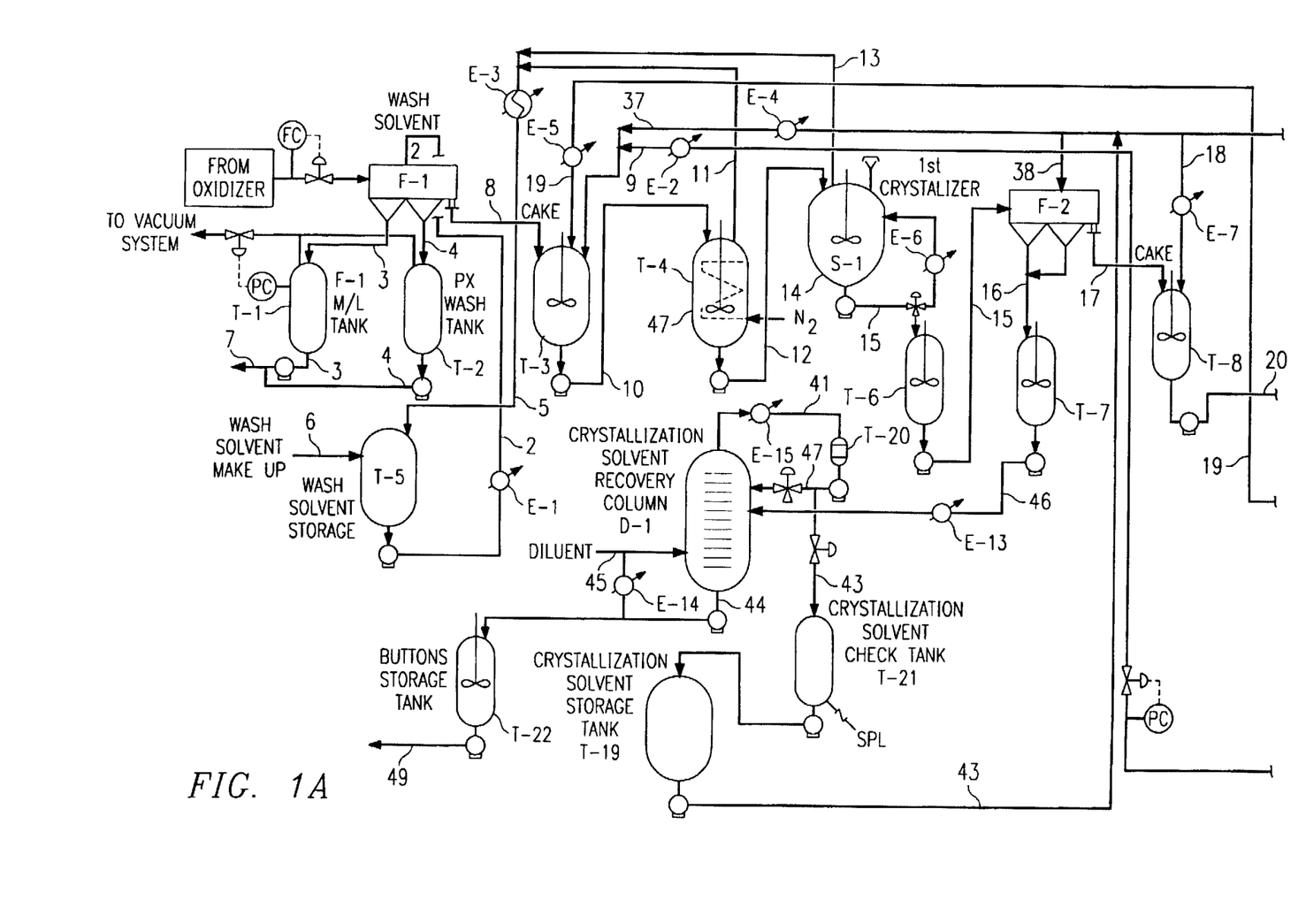
Figure 1B:
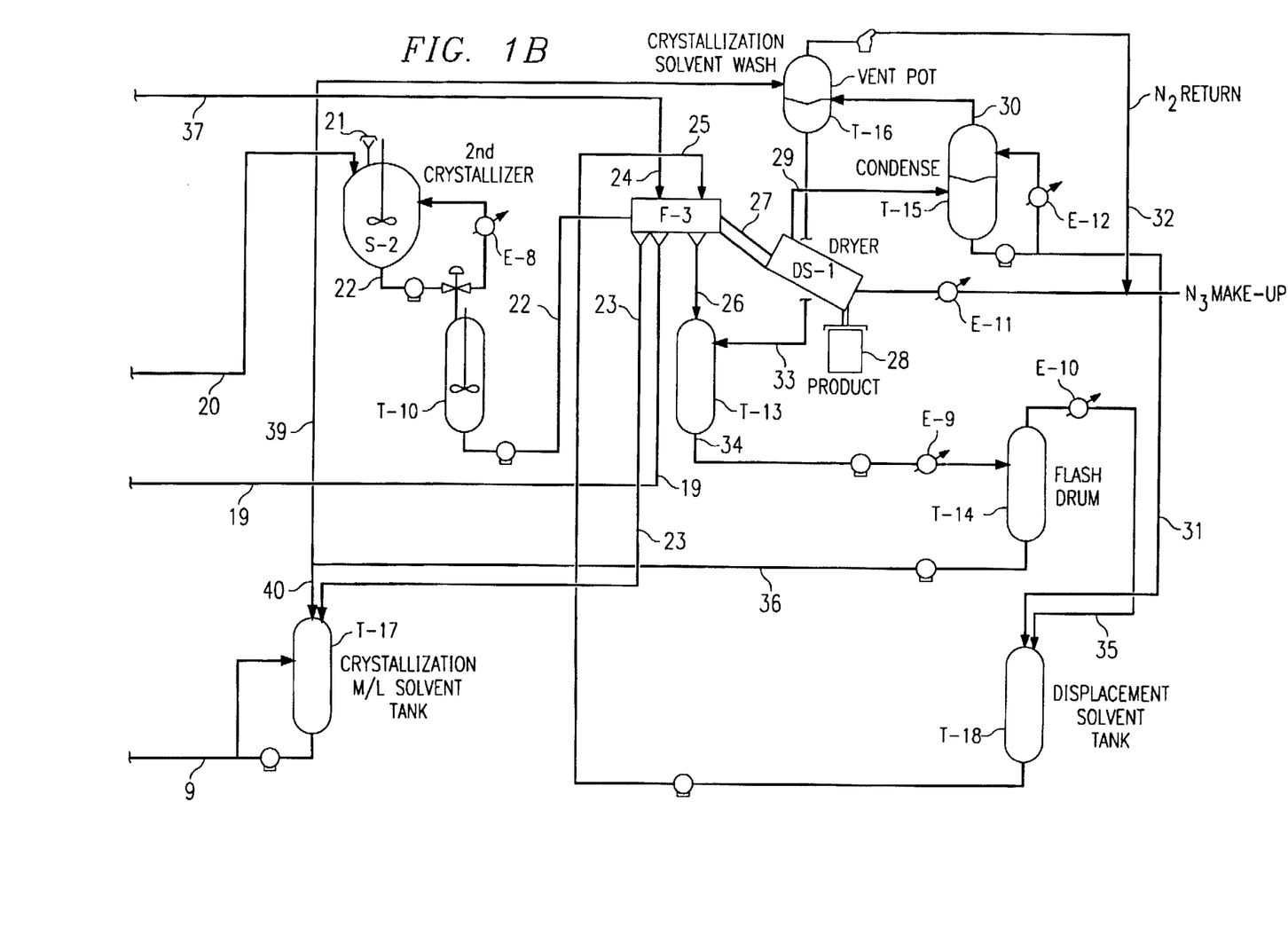

When carrying out the method according to the present invention with the apparatus shown in FIGS. 1A and 1B, employing NMP as the selective crystallization solvent, the present inventors have demonstrated TPA purity levels of up to 99.9+wt % after a first crystallization process, and up to 99.99+wt % after a second crystallization process. In particular, Table 1 illustrates the recovery of 99.95 wt % pure TPA after the first crystallization process and 99.997 wt % pure TPA after the second crystallization process, from crude TPA (89.89 wt % TPA).

TABLE 1

|  | 1st Crystallization | 2nd Crystallization |
|---|---|---|
| (a) Weight of TPA: | 56.34 grams | 31.81 grams |
| (b) Weight of Crystallization Solvent: | 400.02 grams | 248.38 grams |
| (c) Saturation Temperature: | 60° C. | |
| (d) Crystallization Temperature: | 15° C. (one hour) | |

| Benzoic | p-Toluic | 4-CBA | TPA | Others |
|---|---|---|---|---|
| (1) Crude TPA Product Composition: | | | | |
| 0.39 wt % | 4.49 wt % | 2.49 WT % | 89.89 WT % | 274 WT % |

TABLE 1-continued

| (2) First Crystallization Product | | | | |
|---|---|---|---|---|
| 35 ppm | 143 ppm | 359 ppm | 99.95 wt % | Not Detected |
| (3) Second Crystallization Product | | | | |
| <20 ppm | <20 ppm | <10 ppm | 99.997+ wt % | |

Table 2 illustrates the recovery of 99.90 wt % pure TPA after the first crystallization process and 99.9933 wt % pure TPA after the second crystallization process from crude TPA (89.89 wt % TPA) by increasing both the saturation temperature and the crystallization temperature.

TABLE 2

|  | 1st Crystallization | 2nd Crystallization |
|---|---|---|
| (a) Weight of TPA: | 138.08 grams | 70.15 grams |
| (b) Weight of Crystallization Solvent: | 685.30 grams | 247.46 grams |
| (c) Saturation Temperature: | 110° C. | 105° C. |
| (d) Crystallization Temperature: | 40° C. | 40° C. |

| Benzoic | p-Toluic | 4-CBA | TPA | Others |
|---|---|---|---|---|
| (1) Crude TPA Product Composition: | | | | |
| 0.39 wt % | 4.49 wt % | 2.49 wt % | 89.89 wt % | 2.74 wt % |
| (2) First Crystallization Product (Recovery: 56.5 wt %) | | | | |
| 28 ppm | 367 ppm | 390 ppm | 99.90 wt % | 229 ppm |
| (3) Second Crystallization Product (Recovery: 47.5 wt %) | | | | |
| <10 ppm | <19 ppm | 25 ppm | 99.9933 wt % | 13 ppm |

Table 3 illustrates the recovery of 99.9960 wt % pure PTA (single crystallization process) from crude TPA (98.99 wt % TPA). In addition, each of benzoic, p-Toluic, 4-CBA, MMT and other impurities were at less than 10 ppm.

TABLE 3

| (a) Weight of TPA: | 152.67 grams |
|---|---|
| (b) Weight of Crystallization Solvent: | 786.19 grams |
| (c) Saturation Temperature: | 100° C. |
| (d) Crystallization Temperature: | 40° C. |

| Benzoic | p-Toluic | 4-CBA | TPA | MMT | Others |
|---|---|---|---|---|---|
| (1) Crude TPA Product Composition: | | | | | |
| <10 ppm | <10 ppm | 18 ppm | 98.99 wt % | 303 ppm | 0.98 wt % |
| (2) Crystallization Product (Recovery: 50.2 wt %) | | | | | |
| <10 ppm | <10 ppm | <10 ppm | >99.9960 wt % | <10 ppm | <10 ppm |

Table 4 illustrates the recovery of 99.63 wt % pure TPA (single crystallization process) from crude TPA (83.91 wt % TPA) on a large scale basis.

TABLE 4

| (a) Weight of TPA: | 1760 grams |
|---|---|
| (b) Weight of Crystallization Solvent: | 6162 grams |
| (c) Saturation Temperature: | 160° C. |
| (d) Crystallization Temperature: | 50° C. |

TABLE 4-continued

| Benzoic | p-Toluic | 4-CBA | TPA | Others |
|---|---|---|---|---|
| (1) Crude TPA Feed Product Composition: | | | | |
| 1.03 wt % | 4.79 wt % | 5.03 wt % | 83.91 wt % | 5.24 wt % |
| (2) Crystallization Product (Recovery: 24.3 wt %) | | | | |
| 38 ppm | 852 ppm | 0.23 wt % | 99.63 wt % | 500 ppm |

Table 5 illustrates the recovery of 99.92 wt % pure TPA (single crystallization process) from crude TPA (79.79 wt % TPA) on a large scale basis.

TABLE 5

| (a) Weight of TPA: | 1700 grams |
|---|---|
| (b) Weight of Crystallization Solvent: | 5928 grams |
| (c) Saturation Temperature: | 160° C. |
| (d) Crystallization Temperature: | 45° C. |

| Benzoic | p-Toluic | 4-CBA | TPA | Others |
|---|---|---|---|---|
| (1) Crude TPA Feed Product Composition: | | | | |
| 1.59 wt % | 5.19 wt % | 7.61 wt % | 79.79 wt % | 5.81 wt % |
| (2) Crystallization Product (Recovery: 31.5 wt %) | | | | |
| 10 ppm | 203 ppm | 446 ppm | 99.92 wt % | 184 ppm |

Table 6 illustrates the recovery of 99.15 wt % pure TPA (single crystallization process) from crude TPA (83.90 wt % TPA) on a large scale basis at a higher saturation temperature of 190° C.

TABLE 6

| (a) Weight of TPA: | 1965 grams |
|---|---|
| (b) Weight of Crystallization Solvent: | 5684 grams |
| (c) Saturation Temperature: | 190° C. |
| (d) Crystallization Temperature: | 40° C. |

| Benzoic | p-Toluic | 4-CBA | TPA | Others |
|---|---|---|---|---|
| (1) Crude TPA Feed Product Composition: | | | | |
| 1.23 wt % | 5.25 wt % | 6.34 wt % | 83.90 wt % | 3.28 wt % |
| (2) Crystallization Product (Recovery: 48.9 wt %) | | | | |
| — | 0.14 wt % | 0.61 wt % | 99.15 wt % | 0.1 wt % |

Table 7 illustrates the recovery of 99.9915 wt % pure TPA from crude TPA (98.50 wt % TPA) on a large scale basis. The supersaturation of the crystallization mixture resulted in the formation of substantially larger TPA crystals than those crystals resulting from the processes summarized above. As would be understood by one skilled in the art, the sizes of TPA crystals are an important consideration with respect to separation thereof from solvents and impurities.

TABLE 7

| (a) Weight of TPA: | 2333 grams |
|---|---|
| (b) Weight of Crystallization Solvent: | 5698 grams |
| (c) Saturation Temperature: | 160° C. |
| (d) Crystallization Temperature: | 45° C. |

TABLE 7-continued

| Benzoic | p-Toluic | 4-CBA | TPA | Others |
|---|---|---|---|---|
| (1) Crude TPA Feed Product Composition: | | | | |
| 198 ppm | 0.15 wt % | 1.23 wt % | 98.50 wt % | 989 ppm |
| (2) Crystallization Product (Recovery: 69.7 wt %) | | | | |
| <10 ppm | 26 ppm | 38 ppm | 99.9915 wt % | 11 ppm |

According to the invention and as can be seen in the process flow diagrams of FIGS. 1A and 1B, a preferred embodiment of the process is divided into five sections:

(1) Oxidation Section:

In this section, p-xylene is oxidized according to the following main reactions:

(a) p-xylene+oxygen→terephthalic acid (b) p-xylene+oxygen→acid (c) p-xylene+oxygen→4-carboxybenzaldehyde (4-CBA)

The oxidizer residence time is approximately five hours. Since the oxidizer effluent will contain up to about 30% TA, mixing in the oxidizer is very important in order to maintain the yield and selectivity, and to prevent fouling and blockages. The initial mixing of the feed streams may be achieved in a static mixer (outside of the oxidizer). Further mixing may be provided by an air sparger and by external circulation. Depending on the thoroughness of the p-xylene washing step at the filter (discussed below), the terephthalic acid (TA) in the solid can vary frombetween about 55% and about 90+%.

(2) Crystallization Section:

(A) First Crystallization

After filtration, the solids from the oxidizer effluent are mixed with the mother liquor and the solvent wash liquid from the second-stage crystallizer and with additional crystallization solvent. The mixed slurry is dissolved in a slurry tank at a predetermined temperature, preferably at from between about 140° C. and about 190° C. The saturated solution is transferred to a holding tank to remove p-exylene through evaporation. The saturated solution is then fed to the first-stage batch crystallizer to recover purified TA. After the crystallization step, the crystallizer content is then dropped to a product holding tank and is pumped continuously to a filter (or centrifuge) to collect the solids to be recrystallized in the second-stage crystallizer for further purification.

(B) Second Crystallization

The solids generated from the first crystallizer filter are redissolved in a feed dissolver with the crystallization solvent for the second-stage crystallizer at a predetermined condition, such as at a temperature of from between about 140° C. and about 190° C. The saturated solution is pumped to the second-stage crystallizer for crystal growth and recovery. Then, the crystallizer content is dropped to a holding tank for final filtration and drying steps. In the filtration step, the solid (cake) is first washed by the crystallization solvent to displace mother liquor remaining in the cake. The solid is then washed by a low-boiling solvent to displace the crystallization solvent in the cake. The wet cake is sent to the dryer to remove the final liquid from the PTA product.

(3) Mother Liquor/Solvent Recovery Section:

The mother liquor from the first crystallizer filter is transferred to a solvent recovery column to recover the crystallization solvent from the column overhead. The impurities, such as, but not intended to be limited to, p-toluic acid, benzoic acid, 4-carboxybenzaldehyde (4-CBA), and the like, are recovered from the bottom of the column. In order to make sure the column bottom slurry can be transferred back to the oxidizer, a high-boiling diluent is preferably added to the reboiler.

II. Detailed Process Description and Example

The process flow diagram of FIGS. 1A and 1B will be described in terms of the production and recovery of 65 kilograms per hour of terephthalic acid (TA) from the air oxidation of p-xylene in the presence of a solution of components of catalysis in dimethyl terephthalate (DMT) or in a benzoic acid-water solvent system. The oxidizer temperature is preferably between about from 150° C. and about 250° C. and the pressure is from between about 5 and about 10 kg per cm$^2$. Since the oxidizer effluent will contain up to 30% TA, mixing in the oxidizer is very important in order to maintain the yield and selectivity, and to prevent fouling and blockages. The initial mixing of the feed streams may be achieved in a static mixer (outside of the oxidizer). Further mixing may be provided by air sparging and external circulation. In the preferred form of the process about 0.001–0.05 kg per hour of manganese acetate and about 0.003–0.010 kg per hour of cobalt acetate in aqueous solution are fed to the oxidizer to catalyze the oxidation reactions.

The effluent from the oxidizer (483.7 kg/hr) at about 160° C. is transferred through line 1 to filter F-1 to separate the solid from mother liquor (filtrate). In filter F-1, the solid cake is washed with 250.0 kg per hour of p-xylene which is heated by heater E-1 from 30° to 100°–150° C. The mother liquor (281.4 kg/hr) from filter F-1 is transferred via line 3 to tank T-1. The cake washing liquid from filter F-1 (306.9 kg/hr) is removed separately from the filter through line 4 to tank T-2.

The washed cake from filter F-1 is dropped into a slurry tank T-3 through line 8 to mix with the following streams:

Stream 19: 67.9 Kg per hour of NMP (selective crystallization solvent) wash liquor from filter F-3 (heated from 45° to 100°–150° C. by Heater E-5)

Stream 9: 329.3 Kg per hour of mother liquor from tank T-17 (heated from 50° to 100°–150° C. by heater E-2)

Stream 37: 43.5 Kg per hour of NMP from tank T-19 (heated from 45° to 100°–150° C. by heater E-4)

The above mixture (586.1 kg/hr) from tank T-3 is then transferred from the bottom of the tank through line 10 to dissolver T-4. The content in tank T-4 is heated indirectly from 100°–150° C. to 140°–190° C. by a hot oil heating coil in the tank. About 75% of the p-xylene (32.8 kg/hr) and 100% of the sparging nitrogen (10 kg/hr) in the mixture is vaporized from the dissolver and is removed through line 11. Sparging nitrogen is added to tank T-4 via line 47 to assist the removal of p-xylene. Vapor Streams 11 and 13 are combined into stream 5 (51.6 kg/hr), condensed by cooler E-3, and sent to PX Storage tank T-5. The bottom effluent from dissolver T-4 is transferred to crude crystallizer S-1 batchwise.

The batch content in crude crystallizer S-1 is cooled from 140°–190° C. to 10°–20° C. by an external cooler E-6, to generate the desired super-saturation for TA crystals to grow. To improve the crystal size distribution and solid recovery, crystal seeding may be helpful. At the conclusion of a batch crystallization cycle, the slurry is dropped into tank T-6 and transferred to filter F-2 continuously at a rate of 544.6 kg per hour through line 15.

At filter F-2, 42.7 kg per hour of NMP (from line 38) is used to wash the cake. The mother liquor plus NMP wash are combined into stream 16 (432.6 kg/hr) to be fed to the NMP recovery column D-1. The washed cake (154.7 kg/hr) is dropped into dissolver tank T-8 where it is mixed with 241.3 kg per hour of NMP to form the super-saturated feed for pure crystallizer S-2. NMP is heated from 45° C. to 140°–190° C. by heater E-7 and is fed to tank T-8 through line 18.

The content of tank T-8 is transferred batchwise to pure crystallizer S-2 where the temperature is cooled from 140°–190° C. to 30°–60° C. to induce TA crystal growth. The cooling is provided by circulating the crystallizer content through an external Cooler E-8. Again, to improve the crystal size distribution and crystal recovery, crystal seeding may be helpful. At the end of the batch cycle, the slurry is dropped from crystallizer S-2 into tank T-10 (feed tank for Filter F-3).

The slurry is fed to filter F-3 continuously through line 22 at a rate of 395.9 kg per hour. The mother liquor from the filter (301.8 kg/hr) is transferred to tank T-17 via line 23. The cake is initially washed with NMP at 45° C. to displace the remaining mother liquor from the cake, and then the cake is washed with the low-boiling displacement solvent, such as methanol, to displace NMP from the cake. From T-19, the NMP wash is added through line 24 and, from T-18, the displacement solvent is added through line 25 to F-3 (both at a rate of 64 kg/hr). The NMP wash liquid (67.9 kg/hr) is sent to tank T-3 (F-1 slurry tank) through line 19, while the displacement solvent (64.1 kg/hr) is transferred to tank T-13 through line 26.

The washed cake from filter F-3 (90.2 kg/hr) is dropped through line 27 to product dryer DR-1 where displacement solvent in the cake is removed by heating and purging with a counter-current flow of heated nitrogen. The dried PTA product (65.2 kg/hr) is removed from the dryer via line 28 and is stored in the product bin.

Displacement solvent, saturated with nitrogen (76.4 kg/hr) from product dryer DR-1, is vented from the dryer through line 29 to condenser T-15 where the gas mixture is cooled to 25°–45° C. by circulating through the cooler E-12. The condensed displacement solvent (21.2 kg/hr) is transferred to displacement solvent tank T-18, while the non-condensing gas (55.2 kg/hr) is exited from T-15 via line 30 to vent pot T-16. Approximately 2.4 kg per hour of NMP is fed to vent pot T-16 via line 39 to trap displacement solvent in stream 30 (3.8 kg/hr). The trapped displacement solvent, plus NMP (6.1 kg/kr), is transferred to tank T-13 through line 33. Nitrogen removed from T-16 (51.4 kg/hr) is sent back to the dryer by a blower through line 32 and through heater E-11 (to heat the stream from 25° C. to 80°–120° C.).

The bottom stream from tank T-13 (70.2 kg/kr—mixture of NMP and displacement solvent) is transferred through line 34 and heater E-9 (to heat the stream from 25° C. to 80°–120° C.) to displacement solvent evaporator T-14. The displacement solvent vapor from the overhead of T-14 (42.7 kg/hr) is condensed by condenser E-10 and sent to displacement solvent tank T-18 via line 35. The bottom stream from T-14 (27.5 kg/hr) is split into two streams: stream 39 (2.4 kg/hr) to vent pot T-16; and stream 40 (25.1 kg/hr) to filter F-3 mother liquor tank T-17.

The mother liquor and NMP wash from filter F-2 are transferred to tank T-7 through line 16 and then are fed to the NMP recovery column D-1. This stream (432.6 kg/hr) is heated from 15°–25° C. to 130°–170° C. by heater E-13 before entering column D-1. The overhead vapor (433.3 kg/hr) is condensed through condenser E-15 and sent to condensate Pot T-20 via line 41. A part of the condensate (39.4 kg/hr) at 160°–220° C. is returned to the column as the reflux through line 42. The rest of the overhead product from column D-1 (393.9 kg/hr) is sent to the NMP check tank T-21 via line 43. From tank T-21, the regenerated NMP is pumped to the NMP storage tank T-19.

In order to make sure the slurry in Column D-1 Reboiler can be transferred back to the oxidizer, 20 to 60 kg per hour of high-boiling diluent, such as benzoic acid or DMT, is added to the reboiler through line 45. The slurry plus the high-boiling diluent (78.8 kg/hr) is withdrawn from the bottom of column D-1 and is sent back to the oxidizer through line 49.

Although a preferred embodiment of the method and apparatus of the present invention has been illustrated in the accompanying Drawings and described in the foregoing Detailed Description, it will be understood that the invention is not limited to the embodiment disclosed, but is capable of numerous rearrangements, modifications and substitutions without departing from the spirit of the invention as set forth and defined by the following claims.

What is claimed is:

1. A method for purifying crude terephthalic acid from a liquid dispersion thereof also containing impurities selected from unreacted starting materials, solvents, products of side reactions and/or other undesired materials comprising:

filtering said dispersion to form a crude terephthalic acid filter cake;

dissolving said filter cake in a selective nonaqueous, nontoxic and noncorrosive crystallization solvent at an elevated temperature of from between about 140° C. and about 190° C. to form a solution;

crystallizing purified terephthalic acid from said solution in said nonaqueous, nontoxic and noncorrosive crystallization solvent by reducing the temperature of said solution; and separating said crystallized purified terephthalic acid from said solution;

said purified terephthalic acid being produced in the absence of any oxidation step and containing not more than 25 ppm of 4-carboxybenzaldehyde.

2. A method in accordance with claim 1 in which said dispersion contains 4-carboxybenzaldehyde.

3. A method in accordance with claim 1 in which the temperature of said solution is reduced to from between about 5° C. and about 50° C.

4. A method in accordance with claim 3 in which the temperature of said solution is reduced to from between about 10° C. and about 20° C.

5. A method in accordance with claim 1 in which said crystallization of purified terephthalic acid from solution in said selective nonaqueous, nontoxic and noncorrosive crystallization solvent is repeated by redissolving said crystallized purified terephthalic acid in said selective nonaqueous, nontoxic and noncorrosive crystallization solvent to form a redissolved solution at an elevated temperature; and crystallizing purified terephthalic acid from said redissolved solution in said selective nonaqueous, nontoxic and noncorrosive crystallization solvent by reducing the temperature thereof.

6. A method in accordance with claim 1 wherein said selective nonaqueous, nontoxic and noncorrosive crystallization solvent is N-methyl pyrrolidone.

7. A method in accordance with claim 1 wherein said selective nonaqueous, nontoxic and noncorrosive crystallization solvent is selected from the group consisting of N-alkyl-2-pyrrolidone, N-ethyl pyrrolidone, N-mercaptoalkyl-2-pyrrolidone, N-mercaptoethyl-2-pyrrolidone, N-alkyl-2-thiopyrrolidone, N-methyl-2-thiopyrrolidone, N-hydroxyalkyl-2-pyrrolidone, and N-hydroxyethyl-2-pyrrolidone.

8. A method in accordance with claim 1 wherein said selective nonaqueous, nontoxic and noncorrosive crystallization solvent is selected from the group consisting of sulfolane, methyl sulfolane, sulfones, morpholine, N-formyl morpholine, carbitols, $C^1$ to $C^{12}$ alcohols, acetonitrile, adiponitrile, butyronitrile, ethers, amines, amides, and esters.

9. A method in accordance with claim 1 and further comprising the step of washing said filter cake with a wash solvent selected from the group consisting of p-xylene, acetone, methyl ethyl ketone, and methanol.

10. A method in accordance with claim 9 wherein said wash solvent is p-xylene.

11. A method in accordance with claim 1 and further comprising the step of displacing said selective nonaqueous, nontoxic and noncorrosive crystallization solvent subsequent to the step of crystallizing with a displacement solvent selected from the group consisting of methanol, methyl ethyl ketone, and acetone.

12. A method in accordance with claim 1 wherein said displacement solvent is methanol.

13. A method for producing purified terephthalic acid from crude terephthalic acid comprising:

dissolving crude terephthalic acid in a selective nonaqueous, nontoxic and noncorrosive crystallization solvent at an elevated temperature of from between about 140° C. and about 190° C. to form a solution; and crystallizing purified terephthalic acid from said solution at a reduced temperature; said purified terephthalic acid being produced in the absence of any oxidation step.

14. A method in accordance with claim 13 wherein selective nonaqueous, nontoxic and noncorrosive crystallization solvent is N-methyl pyrrolidone.

15. A method in accordance with claim 13 and further comprising the step of separating said purified terephthalic acid from said solution.

16. A method in accordance with claim 15 in which said step of separating is effected by filtering or centrifuging said purified terephthalic acid from said solution, washing it with said selective nonaqueous, nontoxic and noncorrosive crystallization solvent and with a displacement solvent, and thereafter drying it.

17. A method in accordance with claim 13 wherein said selective nonaqueous, nontoxic and noncorrosive crystallization solvent is selected from the group consisting of N-alkyl-2-pyrrolidone, N-ethyl pyrrolidone, N-mercaptoalkyl-2-pyrrolidone, N-mercaptoethyl-2-pyrrolidone, N-alkyl-2-thiopyrrolidone, N-methyl-2-thiopyrrolidone, N-hydroxyalkyl-2-pyrrolidone, and N-hydroxyethyl-2-pyrrolidone.

18. A method in accordance with claim 13 wherein said selective nonaqueous, nontoxic and noncorrosive crystallization solvent is selected from the group consisting of sulfolane, methyl sulfolane, sulfones, morpholine, N-formyl morpholine, carbitols, $C^1$ to $C^{12}$ alcohols, acetonitrile, adiponitrile, butyronitrile, ethers, amines, amides, and esters.

19. A method in accordance with claim 13 wherein said crude terephthalic acid is washed with a wash solvent selected from the group consisting of p-xylene, methanol, acetone and methyl ethyl ketone.

20. A method in accordance with claim 19 wherein said wash solvent is p-xylene.

21. A method in accordance with claim 13 comprising the step of displacing said selective nonaqueous, nontoxic and noncorrosive crystallization solvent subsequent to the step of crystallizing with a displacement solvent selected from the group consisting of methanol, methyl ethyl ketone and acetone.

22. A method in accordance with claim 21 wherein said displacement solvent is methanol.

23. A method for producing purified terephthalic acid from crude terephthalic acid comprising:
dissolving crude terephthalic acid in a selective nonaqueous, nontoxic and noncorrosive crystallization solvent at an elevated temperature of from between about 140° C. and about 190° C. to form a first solution;
crystallizing first stage purified terephthalic acid from said first solution at a reduced temperature;
separating said crystallized first stage purified terephthalic acid from said solution;
redissolving said separated first stage purified terephthalic acid in said selective nonaqueous, nontoxic and noncorrosive crystallization solvent at an elevated temperature to form a second solution;
crystallizing second stage purified terephthalic acid from said second solution at a reduced temperature; and
separating said crystallized second stage purified terephthalic acid from said second solution;
said purified terephthalic acid being produced in the absence of any oxidation step and containing less than 25 ppm of 4-carboxybenzaldehyde.

24. A method in accordance with claim 23 in which said step of separating is effected by filtering or centrifuging said purified terephthalic acid from said solution, washing it with said selective nonaqueous, nontoxic and noncorrosive crystallization solvent and with a displacement solvent, and thereafter drying it.

25. A method in accordance with claim 23 wherein said nonaqueous, nontoxic and noncorrosive crystallization solvent is N-methyl pyrrolidone.

26. A method in accordance with claim 23 wherein said selective nonaqueous, nontoxic and noncorrosive crystallization solvent is selected from the group consisting of N-alkyl-2-pyrrolidone, N-ethyl pyrrolidone, N-mercaptoalkyl-2-pyrrolidone, N-mercaptoethyl-2-pyrrolidone, N-alkyl-2-thiopyrrolidone, N-methyl-2-thiopyrrolidone, N-hydroxyalkyl-2-pyrrolidone, and N-hydroxyethyl-2-pyrrolidone.

27. A method in accordance with claim 23 wherein said selective nonaqueous, nontoxic and noncorrosive crystallization solvent is selected from the group consisting of sulfolane, methyl sulfolane, sulfones, morpholine, N-formyl morpholine, carbitols, $C^1$ to $C^{12}$ alcohols, acetonitrile, adiponitrile, butyronitrile, ethers, amines, amides, and esters.

28. A method in accordance with claim 23 wherein said crude terephthalic acid is washed with a wash solvent selected from the group consisting of p-xylene, methanol, acetone and methyl ethyl ketone.

29. A method in accordance with claim 28 wherein said wash solvent is p-xylene.

30. A method in accordance with claim 23 comprising the step of displacing said selective nonaqueous, nontoxic and noncorrosive crystallization solvent subsequent to said second stage crystallization step with a displacement solvent selected from the group consisting of methanol, methyl ethyl ketone, and acetone.

31. A method in accordance with claim 30 wherein said displacement solvent is methanol.

32. A method for purifying crude terephthalic acid from a liquid dispersion thereof also containing impurities selected from unreacted starting materials, solvents, products of side reactions and/or other undesired materials, said method comprising the steps of:
dissolving crude terephthalic acid in N-methyl pyrrolidone at a temperature of from between about 140° C. and about 190° C. to form a first solution;
crystallizing said dissolved crude terephthalic acid from said first solution at a temperature of from between about 5° C. and about 50° C. to form first stage purified terephthalic acid;
separating said first stage purified terephthalic acid from said first solution by filtration to form a first stage purified terephthalic acid filter cake;
washing said separated first stage purified terephthalic acid filter cake with N-methyl pyrrolidone;
redissolving said first stage purified terephthalic acid filter cake in NMP at is a temperature of from between about 140° C. and about 190° C. to form a second solution;
crystallizing said redissolved first stage purified terephthalic acid from said second solution at a temperature of from between about 5° C. and about 50° C. to form second stage purified terephthalic acid;
separating said second stage purified terephthalic acid from said second solution by filtration to form a second stage purified terephthalic acid filter cake;
washing said second stage purified terephthalic acid filter cake with N-methyl pyrrolidone;
washing said N-methyl Pyrrolidone washed filter cake with methanol; and
drying said second stage purified terephthalic acid filter cake to provide second stage purified terephthalic acid.

33. A method of making purified terephthalic acid comprising the steps of:
contacting p-xylene with oxygen to form crude terephthalic acid in a dispersion thereof also containing impurities selected from unreacted starting materials, solvents, products of side reactions and/or other undesired materials;
dissolving crude terephthalic acid in N-methyl pyrrolidone at a temperature of from between about 140° C. and about 190° C. to form a first solution;
crystallizing said dissolved crude terephthalic acid from said first solution at a temperature of from between about 5° C. and about 50° C. to form first stage purified terephthalic acid;
separating said first stage purified terephthalic acid from said first solution by filtration to form a first stage purified terephthalic acid filter cake;
washing said separated first stage purified terephthalic acid filter cake with N-methyl pyrrolidone;
redissolving said first stage purified terephthalic acid filter cake in N-methyl pyrrolidone at a temperature of from between about 140° C. and about 190° C. to form a second solution;
crystallizing said redissolved first stage purified terephthalic acid from said second solution at a temperature of from between about 5° C. and about 50° C. to form second stage purified terephthalic acid;
separating said second stage purified terephthalic acid from said second solution by filtration to form a second stage purified terephthalic acid filter cake;
washing said second stage purified terephthalic acid filter cake with N-methyl pyrrolidone;
washing said N-methyl pyrrolidone washed filter cake with methanol; and
drying said second stage purified terephthalic acid filter cake to provide second stage purified terephthalic acid.

\* \* \* \* \*

UNITED STATES PATENT AND TRADEMARK OFFICE
CERTIFICATE OF CORRECTION

PATENT NO. : 5,767,311
DATED : June 16, 1998
INVENTOR(S) : Fu-Ming Lee et al.

It is certified that error appears in the above-indentified patent and that said Letters Patent is hereby corrected as shown below:

| | | |
|---|---|---|
| Column 8, line 19 | Before "acid" | Insert --p-toluic-- |
| Column 8, line 40 | Delete "p-exylene" | Insert --p-xylene-- |
| Column 14, line 11 | Delete "is" | |

Signed and Sealed this

Fifteenth Day of December, 1998

Attest:

BRUCE LEHMAN

Attesting Officer

Commissioner of Patents and Trademarks